(12) United States Patent
Yamamoto et al.

(10) Patent No.: US 8,704,512 B2
(45) Date of Patent: Apr. 22, 2014

(54) NONDESTRUCTIVE TESTING SYSTEM FOR STEEL WORKPIECE

(75) Inventors: Yuzo Yamamoto, Tokyo (JP); Ichiro Nagasawa, Osaka (JP)

(73) Assignee: Honda Motor Co., Ltd., Tokyo (JP)

( * ) Notice: Subject to any disclaimer, the term of this patent is extended or adjusted under 35 U.S.C. 154(b) by 695 days.

(21) Appl. No.: 12/934,459

(22) PCT Filed: Mar. 17, 2009

(86) PCT No.: PCT/JP2009/055721
§ 371 (c)(1),
(2), (4) Date: Nov. 11, 2010

(87) PCT Pub. No.: WO2009/119529
PCT Pub. Date: Oct. 1, 2009

(65) Prior Publication Data
US 2011/0062953 A1    Mar. 17, 2011

(30) Foreign Application Priority Data

Mar. 27, 2008 (JP) ................................ 2008-084545
Mar. 27, 2008 (JP) ................................ 2008-084587
Mar. 27, 2008 (JP) ................................ 2008-084622

(51) Int. Cl.
*G01N 27/82* (2006.01)
(52) U.S. Cl.
USPC ........................................................ 324/238
(58) Field of Classification Search
USPC ................. 324/323–337, 342–345, 200, 500; 361/149, 151, 267, 143
See application file for complete search history.

(56) References Cited

U.S. PATENT DOCUMENTS

| 2,245,568 | A | | 6/1941 | Canfield | |
|---|---|---|---|---|---|
| 4,634,976 | A | | 1/1987 | Titto | |
| 6,020,569 | A | * | 2/2000 | Cecil et al. | 219/109 |
| 7,520,800 | B2 | * | 4/2009 | Duescher | 451/527 |
| 2010/0003904 | A1 | * | 1/2010 | Duescher | 451/259 |

FOREIGN PATENT DOCUMENTS

| EP | 1 403 635 | 3/2004 |
|---|---|---|
| EP | 1 574 850 | 9/2005 |
| GB | 1 255 179 | 12/1971 |
| GB | 1255179 | 12/1971 |
| JP | 42-8093 U | 4/1967 |
| JP | 47-6793 U | 2/1972 |
| JP | 62-052451 | 3/1987 |
| JP | 63-044163 | 2/1988 |
| JP | 04-121660 | 4/1992 |
| JP | 07-083883 | 3/1995 |
| JP | 09-089845 | 4/1997 |
| JP | 2004-108873 | 4/2004 |
| JP | 2007-231305 | 9/2007 |

\* cited by examiner

*Primary Examiner* — Melissa Koval
*Assistant Examiner* — Trung Nguyen
(74) *Attorney, Agent, or Firm* — Rankin, Hill & Clark LLP

(57) ABSTRACT

A nondestructive testing system for testing the strength of a gear (15) that has been subjected to vacuum carburization is disclosed. A detection coil (33) embedded in a resin member (32) having a wedge-shaped cross section is placed in proximity to a bottom land (44) of the gear, and the carburized depth of the bottom land is measured to test the strength of the gear.

7 Claims, 10 Drawing Sheets

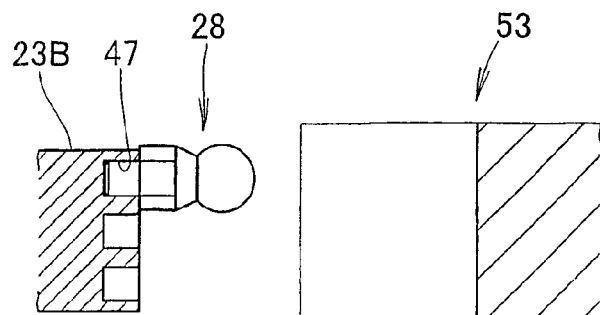
FIG.7
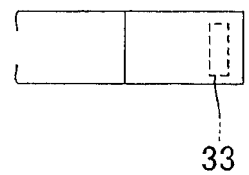
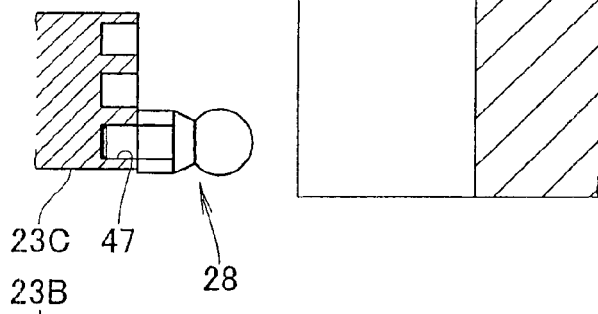
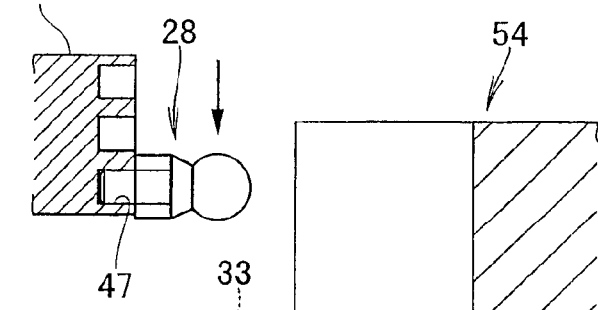
FIG.8
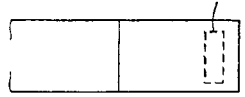
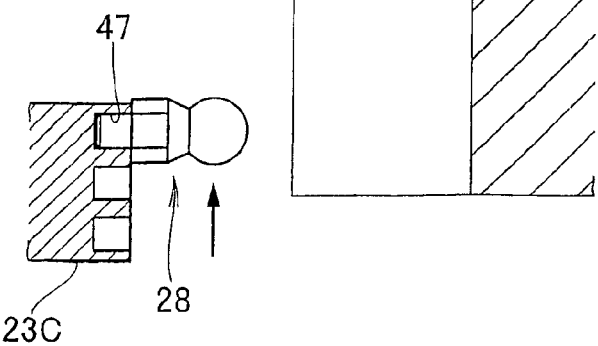

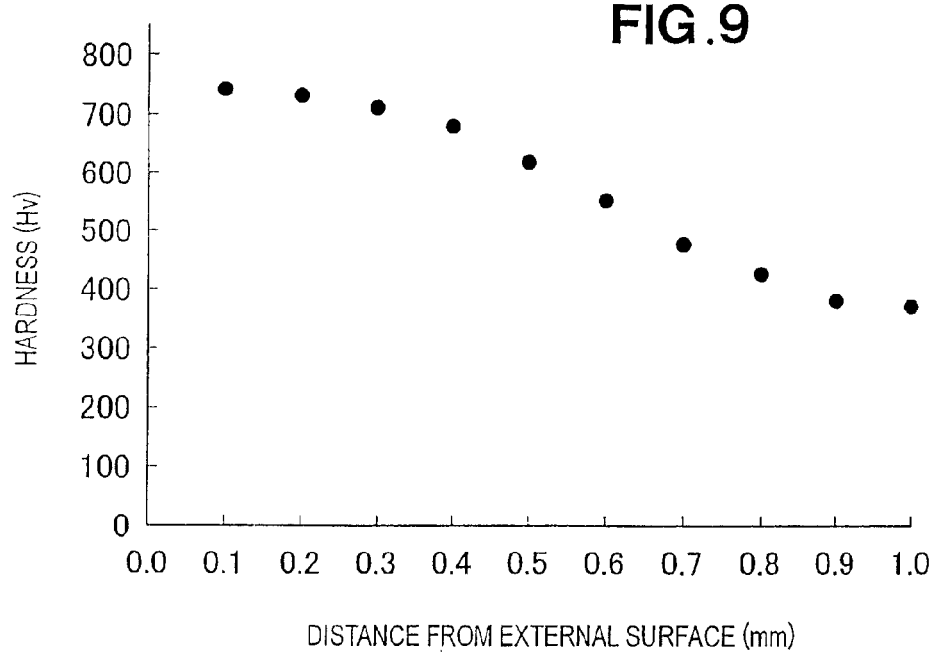
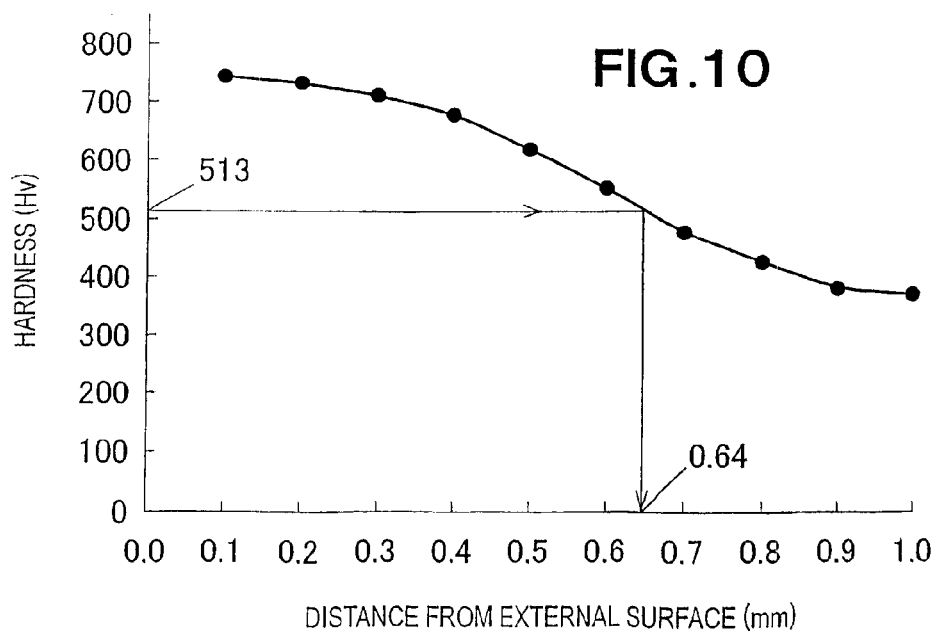

NONDESTRUCTIVE TESTING SYSTEM FOR STEEL WORKPIECE

TECHNICAL FIELD

The present invention relates to a nondestructive testing system for testing a steel workpiece by using the eddy current phenomenon.

BACKGROUND ART

Steel workpieces, as typified by gears, are tested after being manufactured. In this test, only steel workpieces that have passed predetermined acceptability criteria can be advanced to the next step. Nondestructive testing is required in such cases. Such nondestructive testing does not compromise the shapes of the steel workpieces and allows all the workpieces to be tested.

Various apparatuses have been proposed for performing nondestructive testing, one of which is an eddy-current testing apparatus that uses eddy currents, as shown in Japanese Patent Application Laid-Open Publication No. 2004-108873, for example. This eddy-current testing apparatus is described with reference to FIG. 15 hereof.

An excitation coil 102 and a detection coil 103 are wound around a cylindrical steel workpiece 101, as shown in FIG. 15. AC voltage is applied to the excitation coil 102 from an AC power source 104. This causes an eddy current to be generated in the surface layer of the steel workpiece 101. An alternating current is generated in the detection coil 103 by this eddy current. The voltage of this generated alternating current is measured by a measurement device 105. The strength and carburized depth are determined based on this detected voltage.

Voltage is applied to the steel workpiece 101, and since the generated voltage is merely detected based on the eddy current, there is no danger of the steel workpiece 101 being scratched, and the quality can be tested without damaging the workpiece. Therefore, complete testing of the steel workpiece 101 is possible.

Because of the shapes of the excitation coil 102 and detection coil 103, the shape of the steel workpiece 101 is limited to a shaft, a cylinder, or a tube, and application is difficult if the steel workpiece 101 is a flat plate. The application of the eddy-current testing apparatus is thereby limited.

In view of this, there is a need for an eddy-current nondestructive testing apparatus that can be used when the steel workpiece 101 is shaped either as a cylinder or as a flat plate.

The distance L1 from a top land 108L on the left side of a gear 107 to the detection coil 103 should preferably be constant, as shown in FIG. 16. This is because when the distance L1 changes, the detected voltage fluctuates, and measurement precision is reduced. With a manual testing apparatus in which the distance L1 is determined manually, it is difficult to keep the distance L1 constant. With an automatic testing apparatus in which the distance L1 is automatically determined by a robot or the like, the testing apparatus is expensive and large.

In view of this, there is a need for a small and inexpensive nondestructive testing apparatus in which the distance between the tested object and the detection coil can be kept constant.

Furthermore, when the voltage based on the eddy current is detected by a detection coil 103 using the gear 107 as the testing object, the entire external periphery of the gear 107 acts as the testing object for this detected voltage. In other words, information on the top land 111 of the gear 107 and information on the bottom land 112 are combined and harmonized. It is common for defects to readily occur in the bottom land of the gear 107, but when combined information is used, there is a danger that if there are defects in the bottom land 112, these defects will not be detected.

In view of this, there is a need for a nondestructive testing apparatus in which the bottom land 112 alone of the gear 107 can be tested.

DISCLOSURE OF THE INVENTION

According to a first aspect of the present invention, there is provided an apparatus for nondestructive testing of a steel workpiece by using the eddy current phenomenon, which apparatus comprises: an iron core in which rod-shaped arm parts extend in the same direction from both ends of a rod-shaped base part; excitation coils for generating an eddy current in the surface of the steel workpiece, the excitation coils being wound around the two arm parts; a support member located between the excitation coils and extending from the base part; a detection coil for detecting the eddy current, the detection coil being provided at the distal end of the support member; and a conversion device for converting detection information detected by the detection coil into information about the quality of the steel workpiece.

Testing can be performed merely by causing the iron core provided with the excitation coils and detection coil to face the steel workpiece. Since the iron core is merely made to face the steel workpiece, the shape of the steel workpiece may be a plate, a shaft, or a cylinder.

Preferably, the support member is made of a resin.

The testing apparatus can be reduced in weight by using a lightweight resin.

Desirably, the quality of the steel workpiece is expressed as the hardness of the surface of the workpiece or the hardness in an area adjacent to the surface of the workpiece.

The strength of the steel workpiece can be tested by measuring the hardness. Specifically, the testing apparatus can be used to test strength.

Preferably, the steel workpiece is subjected to vacuum carburization.

The strength of the steel workpiece can be tested by measuring the carburized depth. Specifically, the testing apparatus is suitable for a steel workpiece subjected to vacuum carburization.

Desirably, the distal end of the support member has a wedge-shaped cross section so as to be capable of being inserted between two teeth of the gear.

Since the distal end of the support member is wedge-shaped, the support member can be inserted between two teeth of the gear, and the quality of the bottom land of the gear can be tested by the testing apparatus.

Preferably, the testing apparatus is provided with contact members which extend farther from the iron core than the support member and maintain a constant distance from the steel workpiece to the detection coil by being in contact at the distal ends with the steel workpiece.

A constant distance from the steel workpiece to the detection coil can be maintained by the contact members, and measurement precision can be increased.

Desirably, the distal ends of the contact members are spheres.

If the distal ends are spheres, the spheres can be brought into point contact with the steel workpiece.

Preferably, the steel workpiece is a gear.

A gear is an expensive product, and testing via the testing apparatus can guarantee the quality of the expensive gear.

Desirably, the gear is subjected to vacuum carburization.

A carburized gear is an even more expensive product, and testing via the testing apparatus can guarantee the quality of the expensive gear.

Preferably, at least two contact members are provided to the iron core along the width direction of the gear.

If there is a plurality of contact members, slanting in relation to the steel workpiece can be prevented, a constant distance can be maintained from the steel workpiece to the detection coil with a high degree of precision, and measurement precision can be further increased.

Desirably, the contact members are attached to the iron core so as to be capable of moving in the width direction of the gear.

The contact members are moved according to the size of the gear, and particularly according to the gear width. Numerous gears of different shapes can be tested with one testing apparatus, and the effectiveness of the testing apparatus can be increased.

According to a second aspect of the present invention, there is provided a method for nondestructive testing of a steel workpiece wherein a gear as the steel workpiece that has been subjected to vacuum carburization is tested using the eddy current phenomenon, which method comprises the steps of: generating an eddy current in a bottom land of the gear by excitation coils; detecting the eddy current by a detection coil; converting the detected eddy current into a carburized depth by a conversion device; and determining that the steel workpiece is an unacceptable product when the obtained carburized depth is outside of a preestablished range of acceptable depths.

Specifically, the bottom lands are tested to test a gear. In a gear that has been subjected to vacuum carburization, the bottom lands are likely to have a smaller carburized depth than the other areas. In comparison with testing methods for testing the entire periphery of a gear, including top lands, unacceptable products can be specified more reliably according to the present invention, wherein the bottom lands are tested. The result is that the testing can be made more reliable.

Preferably, testing is performed on all of the bottom lands of the gear.

Because of this so-called complete testing, the testing can be made more reliable.

Desirably, the gear is cut, the hardness corresponding to the depth from the external surface is measured in the cut surface to find the correlation between the carburized depth and the hardness, and the carburized depth is determined by the conversion device to make it possible to determine the hardness corresponding to the carburized depth. There is no need to cut the gear after the correlation has been determined.

According to this aspect, not only can the carburized depth be determined, but hardness can be determined as well.

In a preferred form, the measurement data is data in the form of a curve obtained by plotting a plurality of measured hardness values on a graph in which the horizontal axis represents the distance from the external surface and the longitudinal axis represents hardness, and connecting the plotted points.

The number of hardness values can be limited to a number that can be drawn by using data in the form of a curve. Specifically, the number of measurement points of the measured hardness can be reduced. The result is that testing costs involved in destructive testing can be reduced.

BRIEF DESCRIPTION OF THE DRAWINGS

FIG. 7 is a view illustrating an operation of contact members when the space between them is widened;

FIG. 8 is a view illustrating an operation of the contact members when the space between them is narrowed;

FIG. 9 is a graph obtained by plotting hardness values obtained through measurement;

FIG. 10 is a graph obtained by using a curve to connect the hardness values obtained through measurement;

BEST MODE FOR CARRYING OUT THE INVENTION

Figure 1:
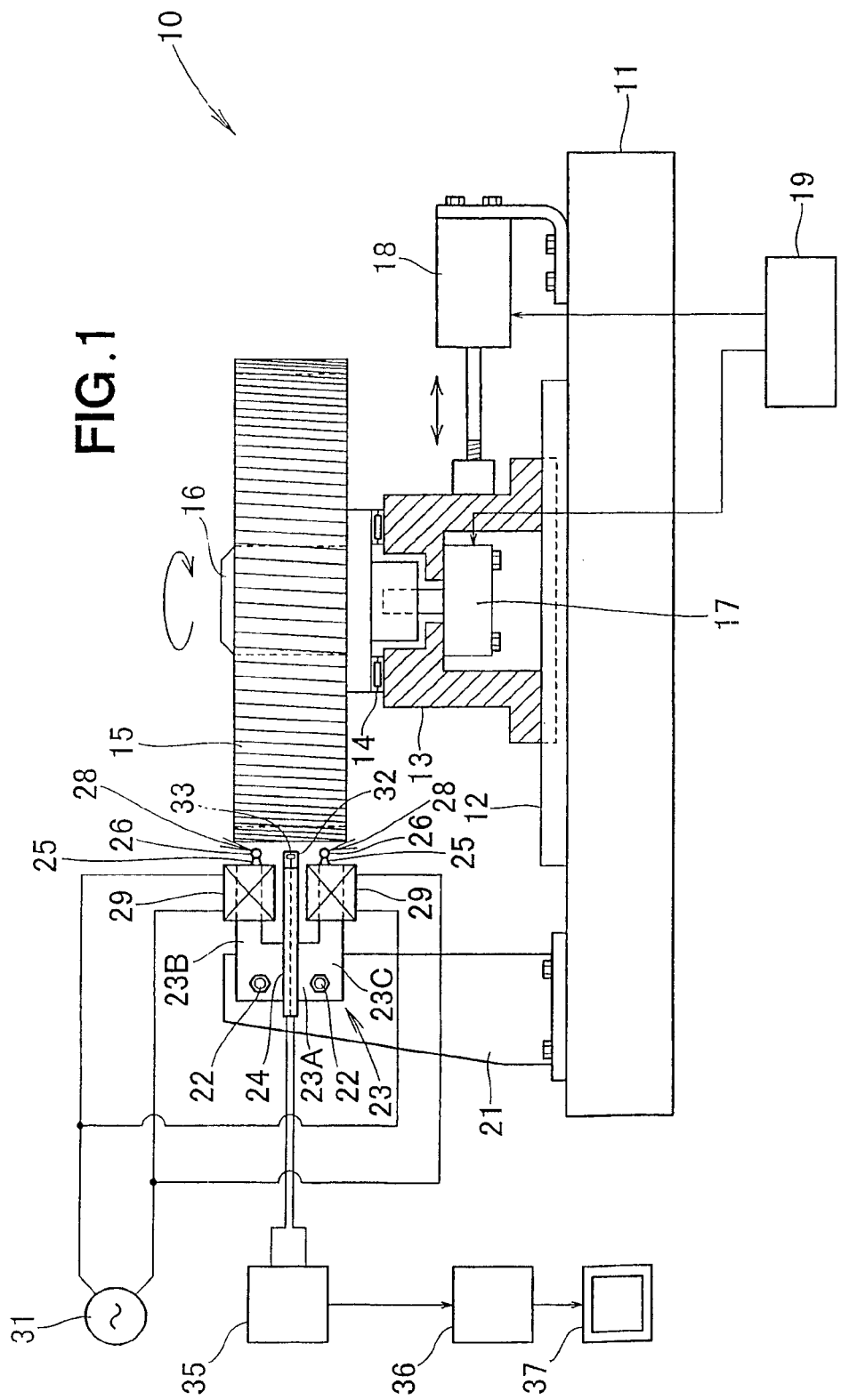
FIG. 1 is a schematic view showing the principle of a nondestructive testing apparatus for a steel workpiece.

A nondestructive testing apparatus 10 for a steel workpiece includes a base 11; a rail 12 provided in the center of the top surface of the base 11 and extending to the left and right of the drawing; a slider 13 placed on the rail 12 and capable of moving left and right; a workpiece support shaft 16 for supporting a gear or another steel workpiece 15, the workpiece support shaft being longitudinally and rotatably supported on the slider 13 via a bearing 14; an index motor 17 for rotating the workpiece support shaft 16 at a constant pitch, the index motor being housed within the slider 13; a cylinder unit 18 for moving the slider 13 back and forth along the rail 12, the cylinder unit being placed on the base 11; a controller 19 for controlling the cylinder unit 18 and the index motor 17; a bracket 21 extending upward from one end (on the left side in the drawing) of the base 11; and an iron core 23 attached to the top of the bracket 21 by bolts 22, 22, as shown in FIG. 1.

The iron core 23 is composed of a rod-shaped base part 23A, and arm parts 23B, 23C extending from one end and the other end of the base part 23A. In a center position between the arm part 23B and the arm part 23C, a support member 24 for supporting a detection coil extends from the iron core 23 toward the steel workpiece 15.

Provided at the distal end of the arm part 23B is a contact member 28 composed of a spherical support part 25 extending toward the steel workpiece 15 and a steel ball or another such sphere 26 provided at the distal end of the spherical support part 25. A contact member 28 is similarly provided to the arm part 23C.

Excitation coils 29, 29 are wound around the arm parts 23B, 23C, and an AC power source 31 for applying AC voltages is joined to the excitation coils 29, 29.

A detection coil 33 is embedded in the distal end of the support member 24. Joined in the following order to the detection coil 33 are a conversion device 35 for acquiring electrical information from the detection coil 33 and converting the information to a carburized depth, an acceptability determination unit 36 for comparing the resulting carburized depth with an acceptable depth to determine if the depth is acceptable, and an acceptability display unit 37 for displaying whether or not the depth is acceptable based on the resulting acceptability determination.

Figure 2:
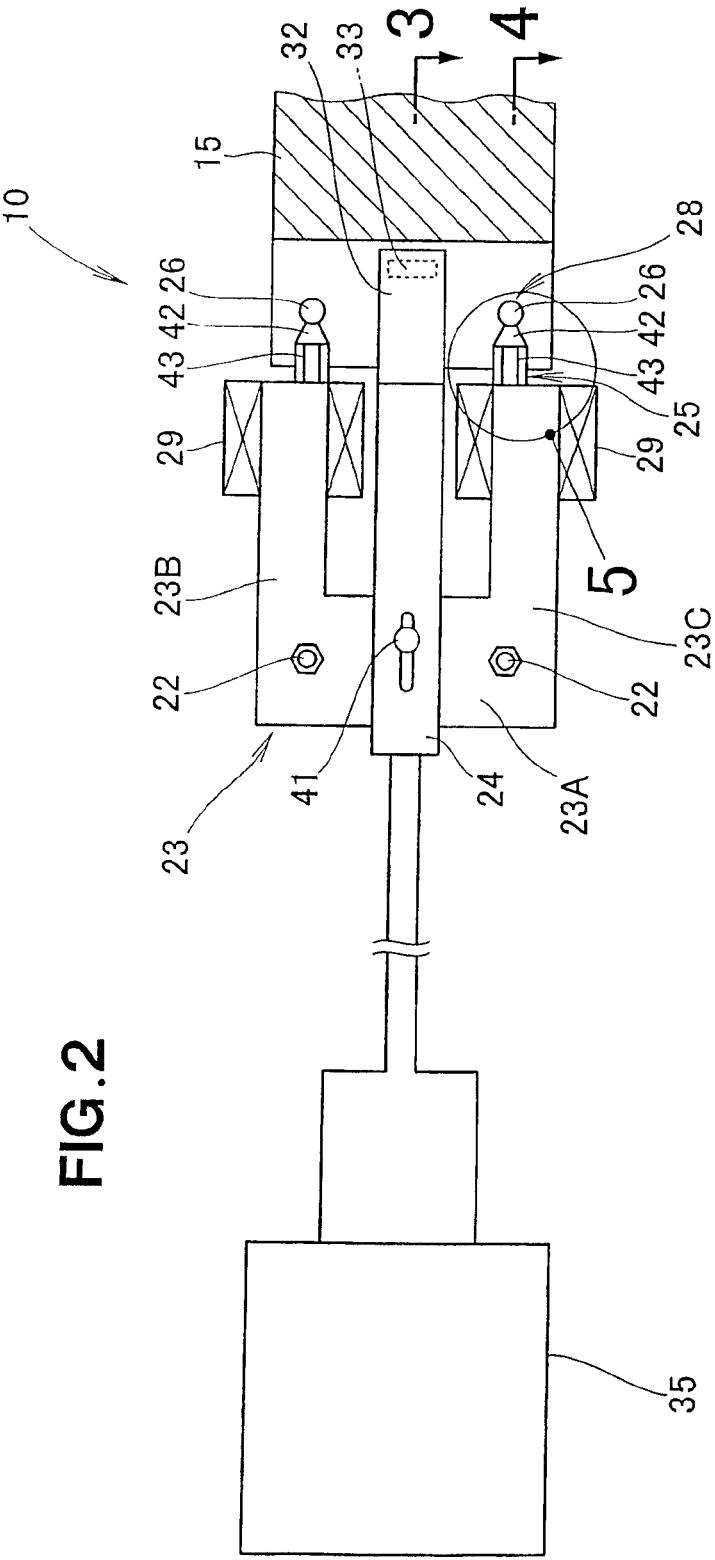
FIG. 2 is a partial enlarged view of the nondestructive testing apparatus for a steel workpiece.

The primary elements of the nondestructive testing apparatus 10 for a steel workpiece include the iron core 23 wherein the rod-shaped arm parts 23B, 23C extend in the same direction from both ends of the rod-shaped base part 23A; the excitation coils 29, 29 for generating an eddy current in the surface of the steel workpiece 15, the excitation coils being wound around the two arm parts 23B, 23C; the support member 24 located between the excitation coils 29, 29 and extending from the base part 23A; the detection coil 33 for detecting the eddy current, the detection coil being provided at the distal end of the support member 24; and the conversion device 35 for converting detection information detected by the detection coil 33 into information about the quality of the steel workpiece 15, as shown in FIG. 2.

Testing can be performed merely by placing the iron core 23 comprising the excitation coils 29, 29 and detection coil 33 so that the core faces the steel workpiece 15. Since the iron core 23 is merely placed facing the steel workpiece 15, the shape of the steel workpiece 15 may be a plate, a shaft, or a cylinder.

Figure 3:
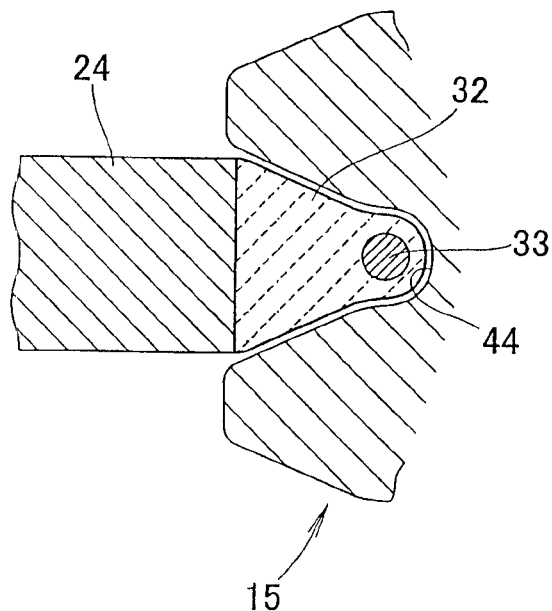
FIG. 3 is a cross-sectional view taken in the direction of arrow 3 of FIG. 2.

The distal end of the support member 24 comprises a resin member 32 having a wedge-shaped cross section or a triangular cross section, as shown in FIG. 3. The detection coil 33 is embedded in the resin member 32.

Since the resin member 32 has a triangular cross section, the resin member can be inserted between the teeth of the gear, and the detection coil 33 can be made to approach the bottom land 44.

The support member 24 may be entirely configured from a resin. This is because the support member 24 is lighter if a lightweight resin is used.

If the steel workpiece 15 is a gear that has been subjected to vacuum carburization, the carburized depth of the gear is smallest (shallowest) at the bottom land 44. If the bottom land is measured where the carburized depth is thinnest, it is possible to know whether or not the gear has a predetermined strength.

Figure 4:
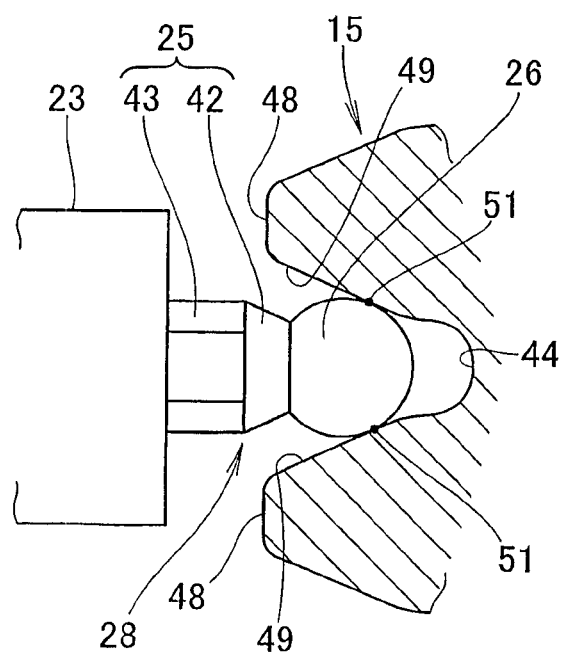
FIG. 4 is a cross-sectional view taken in the direction of arrow 4 of FIG. 2.

Preferably, the spherical support part 25 is composed of a prism-shaped base part 43, and a conical part 42 extending from one end of the base part 43, as shown in FIG. 4. The spherical support part 25 can be rotated in a simple manner by using a spanner on the prism-shaped base part 43.

The spherical diameter of the sphere 26 provided at the tip of the conical part 42 has the outside diameter set so as to meet two conditions, which are a first condition that passage be provided between a top land 48 and an adjacent top land 48, and a second condition that contact be provided with the surfaces of tooth faces 49, 49 before reaching the bottom land 44. Specifically, since the sphere 26 comes in contact at contact points 51, 51, the left-to-right and vertical positions of the sphere in the drawing are defined. In addition, the center of the sphere 26 coincides with the center of the bottom land 44.

As a result, the distance from the bottom land 44 to the detection coil 33 (FIG. 3) or the distance to the excitation coils 29, 29 (FIG. 2) can be made constant. Measurement can be improved by making these distances constant. In other words, a highly reliable steel workpiece testing apparatus is provided.

Furthermore, in cases in which the steel workpiece 15 is a gear, the contact member 28 can be brought into contact between a tooth face 49 and an adjacent tooth face 49 of the gear. By bringing a contact member 28 in contact between a tooth face 49 and another tooth face 49, one contact member can be brought in contact at two points (the numerical symbols 51, 51). This contact at two points makes it possible to stabilize the distance from the gear to the detection coil.

The preferred embodiments of the spherical support part 25 and the arm part 23C will now be described.

Figure 5:
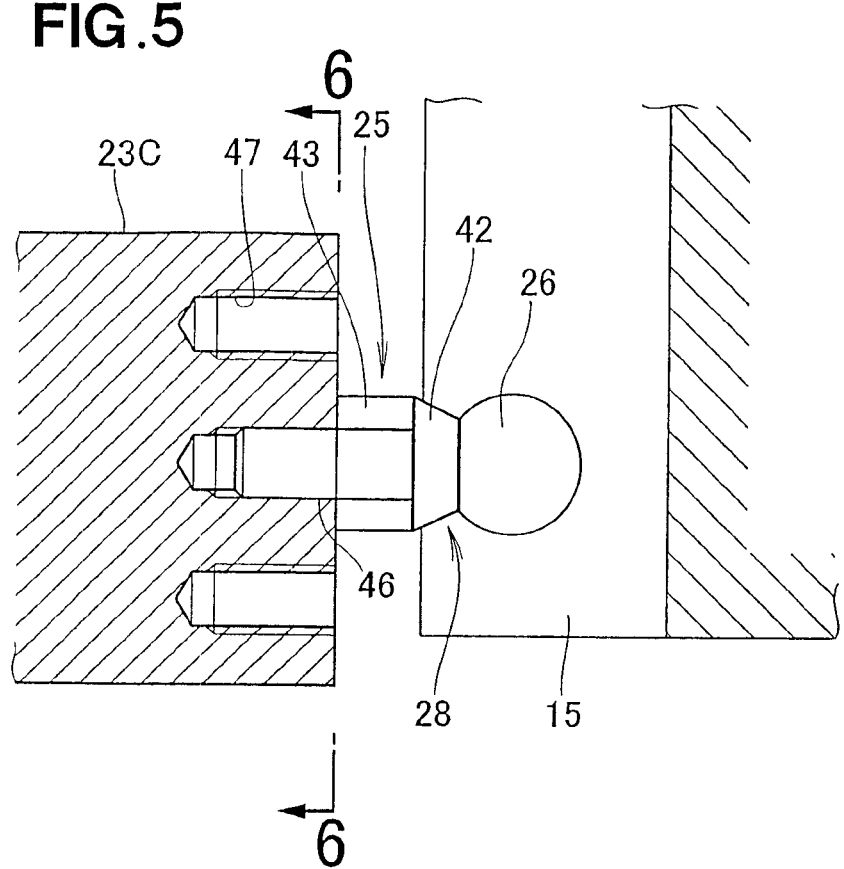
FIG. 5 is an enlarged cross-sectional view of area 5 of FIG. 2.

The base part 43 of the contact member 28 has a hexagonal cross section, and a male screw 46 is formed at the end, as shown in FIG. 5. The male screw 46 screws into a female screw hole 47 formed in the arm part 23C.

Figure 6:
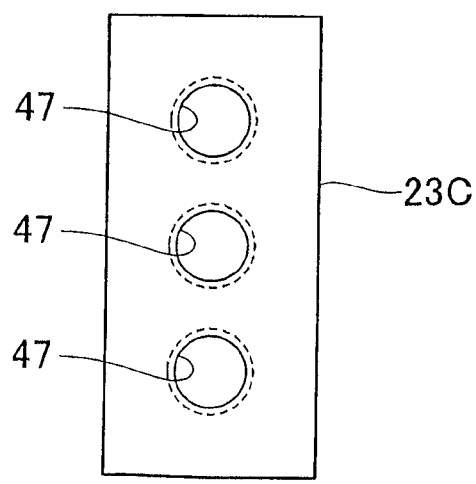
FIG. 6 is a view seen in the direction of arrows 6-6 of FIG. 5.

Three female screw holes 47, for example, are formed in the arm part 23C, as shown in FIG. 6. One female screw hole 47 can be selected from these female screw holes 47 in accordance with the size of the workpiece to be measured, and the contact member 28 (FIG. 4) can be screwed therein.

The following is a description of the operation when there is a plurality of female screw holes 47 formed in the arm part 23C.

When a gear 53 having a large face width is tested, the space between the upper contact member 28 and the lower contact member 28 is widened, as shown in FIG. 7.

In cases in which the size of the gear 53 to be measured changes, the contact members 28 are rotated to remove the contact members 28 from the female screw holes 47.

When a gear 54 having a small face width is tested, the space between the contact member 28 and the lower contact member 28 is narrowed, as shown in FIG. 8.

Specifically, the contact members 28 can be moved in the face width direction of the gear 54, and the contact members 28 can therefore be moved according to the size of the gear 54. The result is that various gears can be measured by one testing apparatus, which is beneficial.

Additionally, in cases in which two contact members 28 are provided along the face width direction of the gear 54, the iron core can be prevented from falling or inclining in relation to the gear 54 by bringing the two contact members 28, 28 in contact with the gear 54.

The conversion device 35 described in FIG. 1 must store a conversion table for converting the measured voltage X into carburized depths.

As part of the storage operation, the frequency was set to 1 kHz using the nondestructive testing apparatus 10 of FIG. 1, and voltage X was measured in a gear that had been subjected to vacuum carburization. Voltage X was −67 mV. This measurement represents a nondestructive test.

Next, the gear was cut, the cut surface was polished, and the carburized depth was then measured. This measurement represents a destructive test. Using the cut surface as an object of measurement, the Vickers hardness (Hv) was measured with a micro-Vickers hardness tester every 0.1 mm up to 1.0 mm from the surface. The measurement results are shown in FIG. 9.

Specifically, FIG. 9 is a graph showing the hardness obtained through measurement, wherein raw data is plotted on a graph, the horizontal axis shows the depth from the surface, and the vertical axis shows the Vickers hardness.

With this type of gear, a required specification is often "a Rockwell C scale hardness of 50 or more at a depth of $\infty$ mm from the surface." A Rockwell C scale hardness of 50 is equivalent to a Vickers hardness (Hv) of 513.

There is no plot corresponding to 513 on the vertical axis gradations. To compensate for this, the plurality of plotted points in FIG. 9 was connected by a smooth curve.

The result is the graph shown in FIG. 10. In this graph, a horizontal line is drawn from 513 on the vertical axis, a vertical line is drawn downward from the point where the horizontal line reaches the curve, and the distance is read at the point where the vertical line reaches the horizontal axis. The distance from the surface was 0.64 mm.

Data based on destructive testing was obtained as described above. In the present invention, electrical signals that accompany an eddy current are registered. With data based on destructive testing, it is important to improve the precision of the electrical signals.

Figure 11:
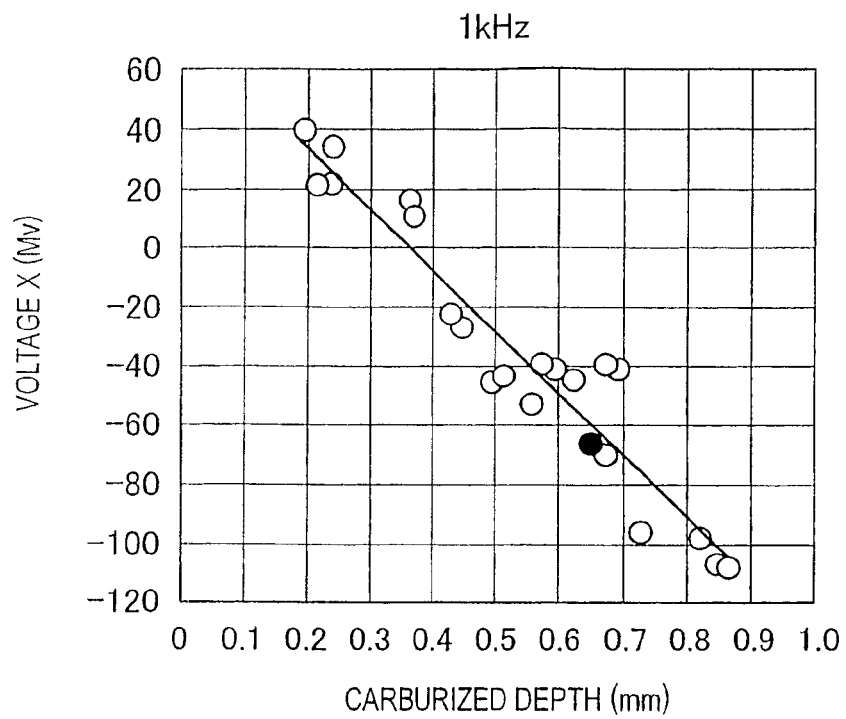
FIG. 11 is a correlation diagram of voltage X and carburized depth.

FIG. 11 is a correlation diagram of voltage X to carburized depth, wherein the horizontal axis shows carburized depth (equivalent to the distance from the surface), the vertical axis shows voltage X, and one data point (0.64 mm, −67 mV) is shown with a solid circle.

Twenty-one samples were prepared by changing the carburization conditions, and the carburized depths and voltages X for these samples were determined by following the same procedure as in FIGS. 9 and 10. The data for the twenty-one samples is shown on the graph with empty circles.

The one solid circle point and the twenty-one empty circle points are distributed along a straight line that extends down and to the right. If voltages X of the vertical axis are obtained through measurement, carburized depths corresponding to the resulting voltages X can be determined from the correlation diagram.

Although the detailed calculation method is not given, the correlation coefficient ($r^2$) in this distribution is 0.92.

If voltage X is determined, the carburized depth can be determined from FIG. 11, and if the carburized depth is determined, the hardness can be determined based on FIG. 10.

Therefore, if voltage X is determined, both the carburized depth and the hardness can be determined.

The present invention has characteristics in the following respects, as is made clear from the above description. Specifically, the resulting hardness and depth are obtained from a curve that connects plotted points representing hardness obtained through measurement in successive points from the surface of the gear toward the center, as shown in FIGS. 9 and 10. Since a curve is obtained by connecting the points, the number of measurement points can be set to a low number, the measurement time can be reduced, and measurement costs can be curtailed.

Next, in order to specify the preferred frequency, the frequency was varied from 700 Hz to 4 kHz, the twenty-two samples were prepared for each frequency, a correlation diagram similar to FIG. 11 was created, and correlation coefficients were determined. The results are shown in the next diagram.

Figure 12:
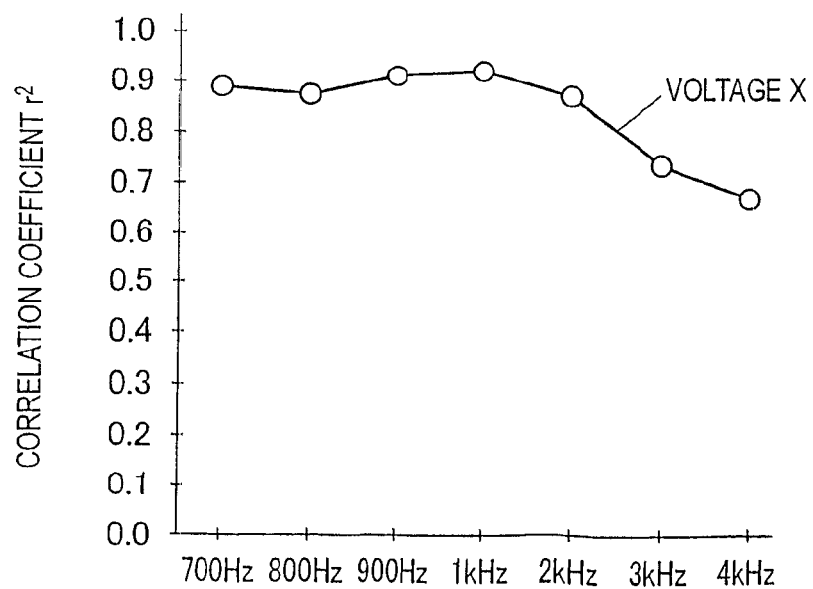
FIG. 12 is a graph showing the relationship between frequency and correlation coefficient.

FIG. 12 is a graph showing the relationship between frequency and correlation coefficient, wherein the correlation coefficient reaches a maximum at 1 kHz, and decreases at 2 kHz and above. The variation in correlation coefficient is small from 700 Hz to 1 kHz.

It was clear that in order to find the carburized depth of a bottom land of the vacuum-carburized gear, the frequency is preferably set to a range of 700 Hz to 1 kHz.

The following is a description of a nondestructive testing method for a steel workpiece in which the eddy current phenomenon is used to test steel workpieces.

Figure 13A:
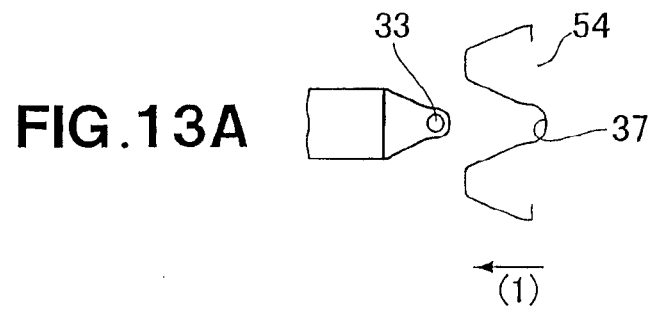
FIGS. 13A through 13D are views illustrating the operation of a nondestructive testing apparatus for a steel workpiece.

First, the gear 54 is moved forward in the direction shown by the arrow (1) toward the static detection coil 33, as shown in FIG. 13A.

Figure 13B:
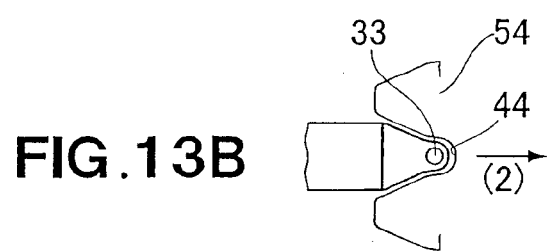

Next, an arbitrary bottom land 44 is made to face the detection coil 33, as shown in FIG. 13B. An eddy current is then generated by the excitation coils in the bottom land 44 of the gear 54. The eddy current is then detected by the detection coils. Next, the detected eddy current is converted to a carburized depth by the conversion device. When the resulting carburized depth is outside of the preestablished range of acceptable depths, it is determined that the steel workpiece is an unacceptable product.

The gear 54 is then moved backward as shown by the arrow (2).

Figure 13C:
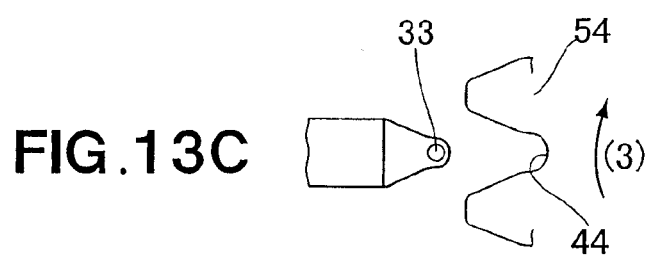
Figure 13D:
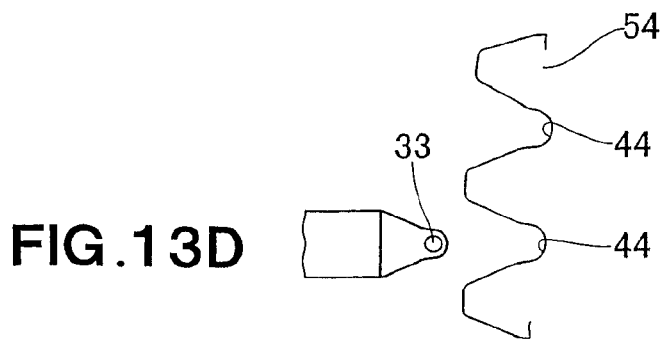

Next, the gear 54 is rotated (in the direction of arrow (3)) by one pitch (proportionate to one tooth) as shown in FIG. 13C. The next bottom land 44 then faces the detection coil 33 as shown in FIG. 13C. The process hereinafter returns to FIG. 13A and the operation continues. This continuing operation is described once again in accordance with the process flow.

Next, the nondestructive testing method for a steel workpiece will be described with reference to a flowchart.

Figure 14:
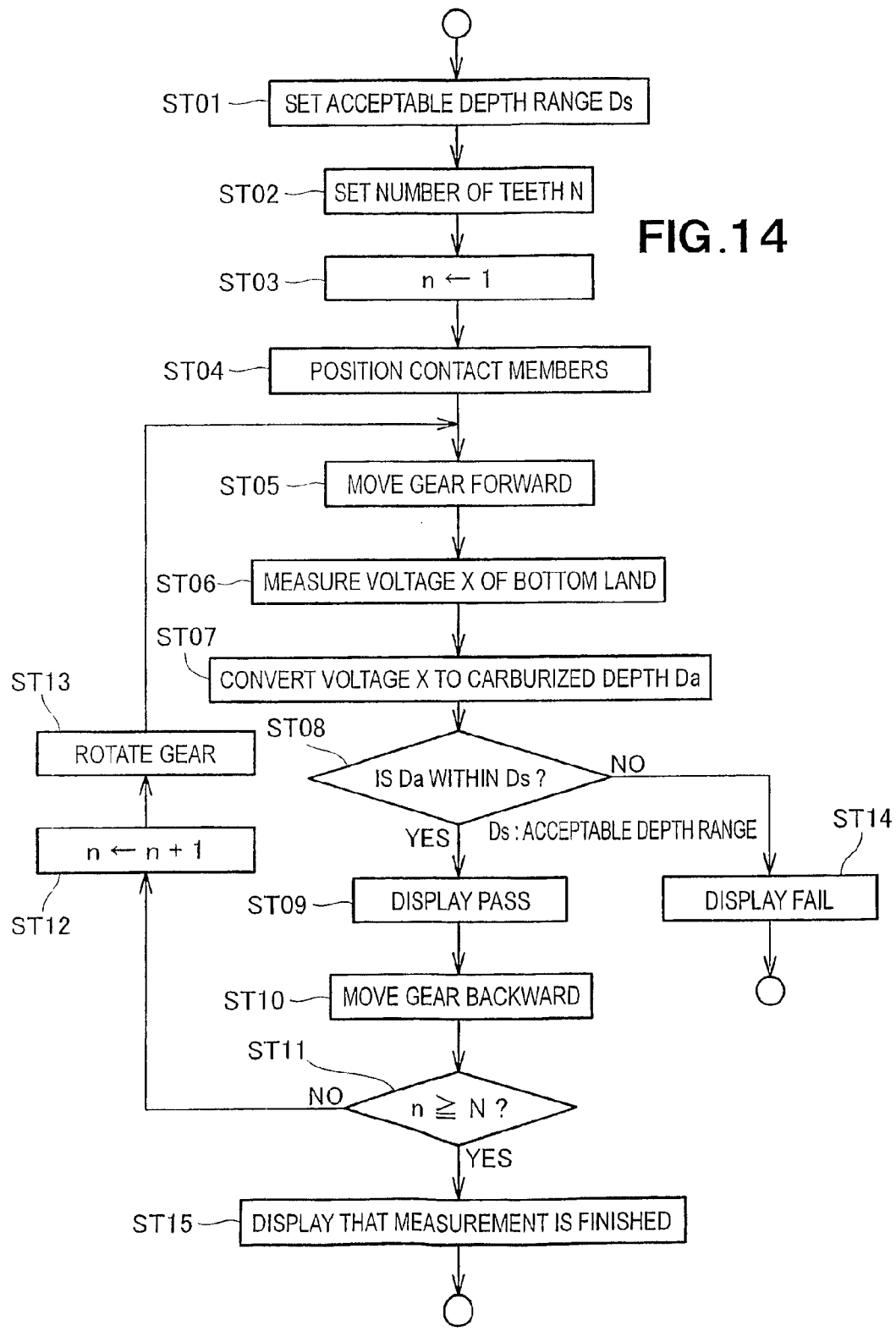
FIG. 14 is a flowchart describing a nondestructive testing method for a steel workpiece.
Figure 15:
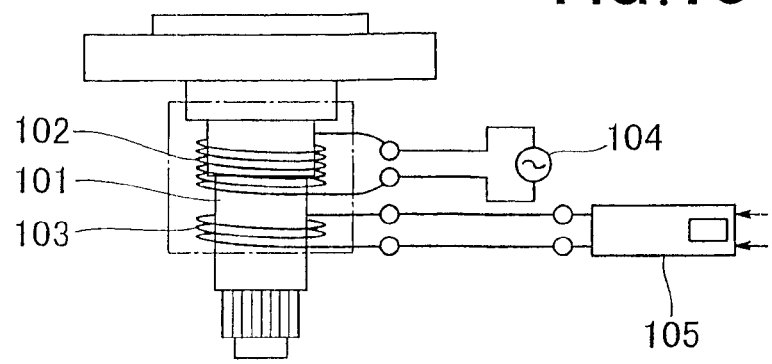
FIG. 15 is a view illustrating the fundamental principles of a conventional technique.
Figure 16:
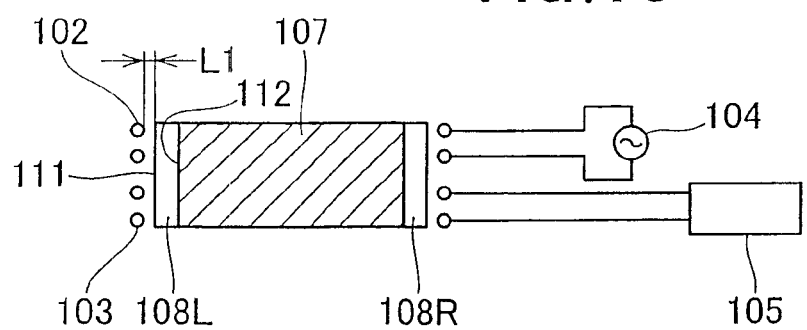
FIG. 16 is a view illustrating the problems with a conventional technique.

In step number (abbreviated as ST) 01, an acceptable depth Ds is established, as shown in FIG. 14. For example, the acceptable depth Ds may be set to 0.5 mm. 0.5 mm is inputted to the acceptability determination unit 36 in FIG. 1.

In ST02, the number of teeth N in the gear to be measured is inputted to the controller 19 in FIG. 1. In order to monitor the number of measurements, a number n is first set to 1 (ST03). Next, the contact members 28 are positioned as shown in FIGS. 7 and 8 (ST04).

When the contact members 28 have been positioned, the gear is moved forward as shown in FIG. 13A (ST05). Voltage X of the bottom land is measured as shown in FIG. 13B (ST06). The X voltage is converted to a carburized depth Da by the conversion device 35 of FIG. 1 (ST07). The acceptability determination unit 36 of FIG. 1 determines whether or not the carburized depth Da obtained through measurement is greater than the acceptable depth Ds (ST08). If the determination is "YES", the word "pass" is displayed (ST09). Next, the gear is moved backward as shown by the arrow (2) in FIG. 13B (ST10).

The number of measurement cycles is then determined (ST11). In the first cycle, n is 1. If the number of teeth N in the gear is 40, for example, the determination is "NO" because n<N, and 1 is added to n (ST12). The gear is then rotated by the equivalent of one tooth as shown in FIG. 13C (ST13). The carburized depth of the bottom land is then measured again starting with ST05.

In ST08, if the carburized depth Da falls below the acceptable depth Ds, the determination is "NO," and a failure is displayed (ST14). In the case of a failure, measurements for this gear can be stopped at this time.

In ST11, if the measurement number n reaches the number of teeth N, this means that all of the bottom lands have been tested, the display shows that measurement is completed, and the measurements are concluded (ST15).

In cases in which there are 40 teeth, there may be cases in which 38 teeth will pass, but the other two teeth will fail. In such cases, a test omission may have occurred in a random test, in which only one tooth per gear is tested. In view of this, a complete testing is needed, in which all of the teeth are tested. According to the present invention, a complete testing of all the teeth can be easily performed.

In the nondestructive testing method for a steel workpiece of the present invention, carburized depth may be measured with an apparatus or tool other than the nondestructive testing apparatus 10 for a steel workpiece shown in FIG. 1. In other words, the form or type of the measurement apparatus is irrelevant as long as the carburized depth of a bottom land can be measured in a nondestructive manner.

INDUSTRIAL APPLICABILITY

The present invention can be used as a technique for measuring the carburized depth of a gear that has been subjected to vacuum carburization.

The invention claimed is:

1. An apparatus for nondestructive testing of a hardened steel workpiece by using eddy current phenomenon, comprising:
    an iron core having a rod-shaped base part and two rod-shaped arm parts extending perpendicularly in a same direction from both ends of the rod-shaped base part;
    two excitation coils for generating an eddy current in a surface of the steel workpiece, the two excitation coils, respectively, being wound around the two arm parts;
    a support member located centrally between the excitation coils and extending from the base part in parallel relation to the arm parts;
    a detection coil for detecting the eddy current, the detection coil being provided at a distal end of the support member; and
    a conversion device for converting electric information detected by the detection coil into information about a hardened depth of the hardened steel workpiece using a conversion table stored therein.

2. The apparatus of claim 1, wherein the support member is made of a resin.

3. The apparatus of claim 1, wherein the hardened steel workpiece is a carburized steel workpiece, and the conversion table is a voltage X-to-carburized depth conversion table previously stored in the conversion device and converting a voltage X of the eddy current detected by the detection coil to a carburized depth of the carburized steel workpiece, and wherein the conversion device further has a carburized depth-to-hardness conversion table previously stored therein and converts the carburized depth of the carburized steel workpiece into a hardness of the surface of the carburized steel workpiece or a hardness in an area adjacent to the surface of the carburized steel workpiece using the carburized depth-to-hardness conversion table.

4. The apparatus of claim 1, wherein the hardened steel workpiece is a gear, and the distal end of the support member has a wedge-shaped cross section for insertion between two adjacent teeth of the gear.

5. The apparatus of claim 1, further comprising:
    two contact members extending farther from distal ends of the respective arm parts of the iron core than the support member, the contact members having distal ends adapted to be in contact with the steel workpiece so as to maintain a constant distance from the steel workpiece to the detection coil.

6. The apparatus of claim 5, wherein the distal ends of the contact members are spheres.

7. The apparatus of claim 5, wherein the contact members are detachably mounted on the distal ends of the arm parts of the iron core such that a distance between the contact members can be changed.

* * * * *